United States Patent [19]

Meswania

[11] Patent Number: 5,387,218
[45] Date of Patent: Feb. 7, 1995

[54] SURGICAL INSTRUMENT FOR SHAPING A BONE

[75] Inventor: Jayantilal M. Meswania, Middlesex, United Kingdom

[73] Assignee: University College London, London, United Kingdom

[21] Appl. No.: 910,017

[22] PCT Filed: Dec. 5, 1991

[86] PCT No.: PCT/GB91/02159
§ 371 Date: Feb. 23, 1993
§ 102(e) Date: Feb. 23, 1993

[87] PCT Pub. No.: WO92/10138
PCT Pub. Date: Jun. 25, 1992

[30] Foreign Application Priority Data

Dec. 6, 1990 [GB] United Kingdom ........... 9026592

[51] Int. Cl.⁶ .................................................. A61F 2/46
[52] U.S. Cl. ................................. 606/80; 606/79; 606/96
[58] Field of Search ................ 606/80, 84, 85, 79, 606/86, 92, 95, 96, 99, 62, 60; 433/165, 166; 408/223, 224, 225, 227, 228

[56] References Cited

U.S. PATENT DOCUMENTS

| | | |
|---|---|---|
| 1,636,636 | 7/1927 | Humble . |
| 4,473,070 | 9/1984 | Matthews . |
| 4,552,136 | 11/1985 | Kenna ............................ 606/85 |
| 4,706,659 | 11/1987 | Matthews . |
| 4,751,922 | 6/1988 | DiPietropolo .................. 606/80 |
| 4,936,862 | 6/1990 | Walker et al. . |
| 5,169,402 | 12/1992 | Elloy ............................. 606/85 |

FOREIGN PATENT DOCUMENTS

| | | |
|---|---|---|
| 0139520 | 5/1985 | European Pat. Off. . |
| 0206777 | 12/1986 | European Pat. Off. . |
| 0253526 | 1/1988 | European Pat. Off. . |
| 0303436 | 2/1989 | European Pat. Off. ........ 606/80 |
| 3209403 | 9/1983 | Germany . |
| 3538654 | 4/1987 | Germany ........................ 606/80 |
| 2236679A | 4/1991 | United Kingdom . |
| 0606578 | 5/1978 | U.S.S.R. ........................ 606/80 |

*Primary Examiner*—Stephen C. Pellegrino
*Assistant Examiner*—Guy V. Tucker
*Attorney, Agent, or Firm*—Lowe, Price, LeBlanc & Becker

[57] ABSTRACT

An instrument for shaping a bone cavity has a frame (2) including a stud (5) for locating the instrument in a bone canal. A curved rod (1) is supported on the frame and a plurality of cutting teeth (18) are threaded on the rod so as to be rotatable thereon. The cutting teeth are drivably interconnected so that rotation of one tooth causes an adjacent tooth to rotate.

10 Claims, 5 Drawing Sheets

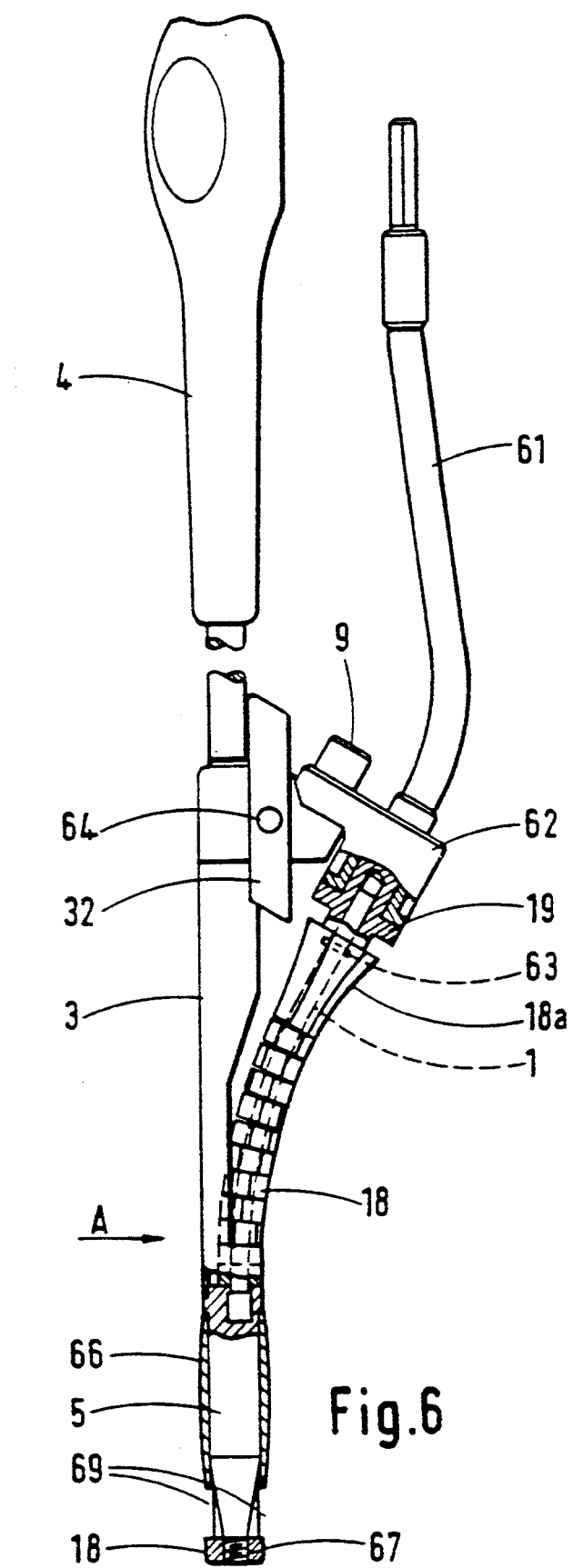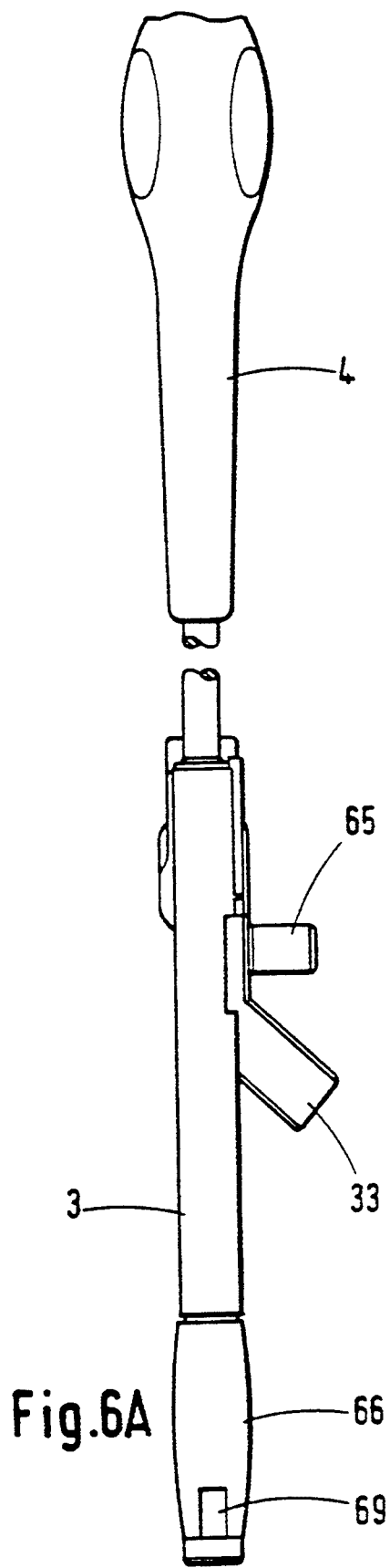

5,387,218

SURGICAL INSTRUMENT FOR SHAPING A BONE

FIELD OF THE INVENTION

This invention relates to surgical instruments and in particular to a reaming tool for shaping bone canals for insertion of surgical implants.

BACKGROUND ART

In recent years surgical implants, e.g. for hip replacement operations, have become more routinely fitted. Current research in the design of hip replacement joints has suggested the desirability of accurate matching of the implant to the internal shape of the bone canal. Conventional practice for cutting and shaping bone canals, preparatory to introduction of a surgical implant, involves use of surgical cutting instruments consisting essentially of a variety of hand-held power drills, saws. reamers and cutters. Satisfactory use of such instruments requires a high degree of manual skill to cut and shape bone canals accurately. A particular difficulty arises where there is a requirement to cut or shape a tapered or curved surface, for example, to shape a bone canal for reception of the stem of a hip implant.

SUMMARY OF THE INVENTION

According to a first aspect of the invention there is provided a surgical instrument for shaping a bone or cavity in a bone which comprises a curved rod whose curvature substantially corresponds in one plane to that of a desired shaped surface, means for supporting the curved rod, a plurality of cutting teeth or heads mounted on said rod so as to be rotatable thereon, said teeth being drivably interconnected so that rotation of one of said teeth causes an adjacent tooth to rotate.

According to a second aspect of the present invention there is provided a surgical instrument, especially for shaping a bore or cavity in a bone, which comprises a curved rod whose curvature substantially corresponds in one plane to that of a desired shaped surface, means for supporting the curved rod, a plurality of cutting teeth or heads threaded on said rod so as to be rotatable thereon, said teeth being drivably interconnected so that rotation of one of said teeth causes the others to rotate.

The curved supporting rod may be mounted in a frame, said frame including a guide for location in or on a suitable reference surface, e.g. within a bore in a bone canal. Conveniently, one end of the row of cutting teeth is connected to a drive attachment for insertion in the chuck of a drill or similar driving mechanism. The tool may also include a handle for manipulating the tool with respect to the bone.

Linking of the teeth together may be achieved by gear-like recesses and projections in adjacent teeth and preferably there is a substantial degree of play in the inter-engaging gear teeth and recesses so that the cutting teeth follow a spiral-like form when they are rotated.

Preferably, the surgical instrument includes one or more depth gauges which are preferably adjustable to determine the amount by which the tool extends into the bone cavity. Preferably, the depth gauge or gauges is adjustable as appropriate for different bones and implants.

In another application of surgical instruments according to the invention, it may be desired to shape a tapered surface in or on a bony, horny or dental surface. For such wider applications, it may not be necessary to cut a surface having a curvature in two planes. In such a case the interengaging teeth may be mounted on a straight rod and the rod may constitute the frame of the tooth.

According to a further aspect of the present invention, therefore, there is provided a surgical instrument which comprises a frame, a rod supported by said frame, a plurality of cutting teeth mounted for rotation on said rod and being mutually engageable, so as to be rotatable in unison when one of said teeth is connected to driving means. Preferably, the teeth have lateral cutting surfaces so that the surface to be shaped or smoothed is contacted substantially at right angles to the direction of the rod. The frame may include a handle and/or guide means for guiding the translation of the instrument in a desired direction.

Further features and advantages of the present invention will become apparent from the accompanying description of one embodiment of a surgical instrument in accordance with the invention, which is illustrated in the attached drawings in which:

BRIEF DESCRIPTION OF THE DRAWINGS

FIG. 6 is a view similar to FIG. 1 of a modified instrument in accordance with the invention, and FIG. 6A is a view taken in the direction of the arrow A in FIG. 6.

DESCRIPTION OF THE PREFERRED EMBODIMENTS

Figure 1:
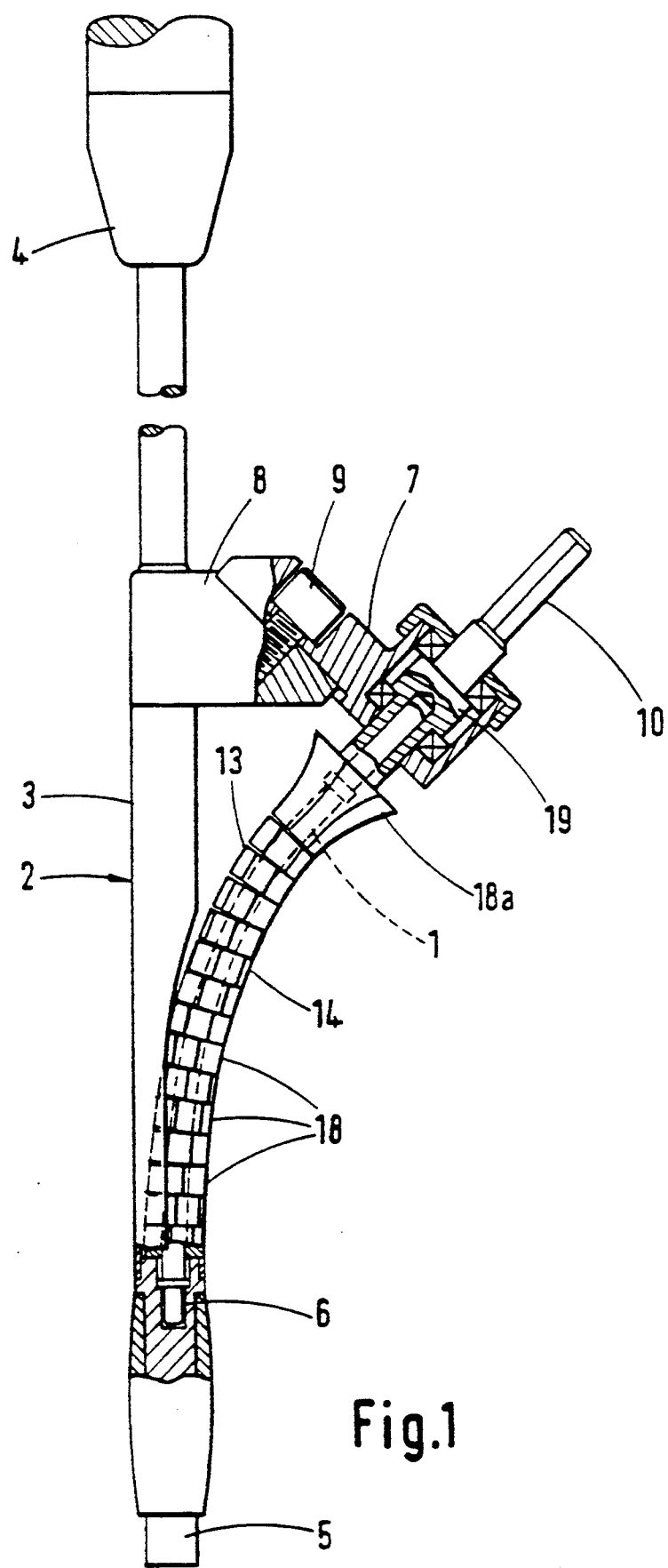
FIG. 1 is a side elevation of the instrument.

Referring to FIG. 1, the tool comprises a curved rod 1 which is fixedly supported in a frame 2 comprising a tubular rod 3, to one end of which is attached a handle 4 and at the other end a cylindrical stud 5. One end of the rod 1 is received in a bore 6 formed in stud 5, while the other end is secured in a bracket 7 which is attached at the upper end of tube 3 via a collar 8 and bolt 9. Threaded onto rod 1 are a series of cutting teeth or heads 18, whose construction is shown in more detail an enlarged scales in FIGS. 2 and 2A. Each of the cutting teeth 18 is drivably engaged with an adjacent tooth and the uppermost tooth 18a is drivably connected through a connector 19 to a drive shaft 10 which can be received in the chuck of a drill or similar prime mover. The teeth 18 may be of the same general size or alternative of some may have slightly different profiles in order to achieve desired shapes in the bone or other material to be shaded. For example, as shown in FIG. 1, the upper cutting tooth 18a. is larger than the rest and has a generally conical form.

Figure 2:
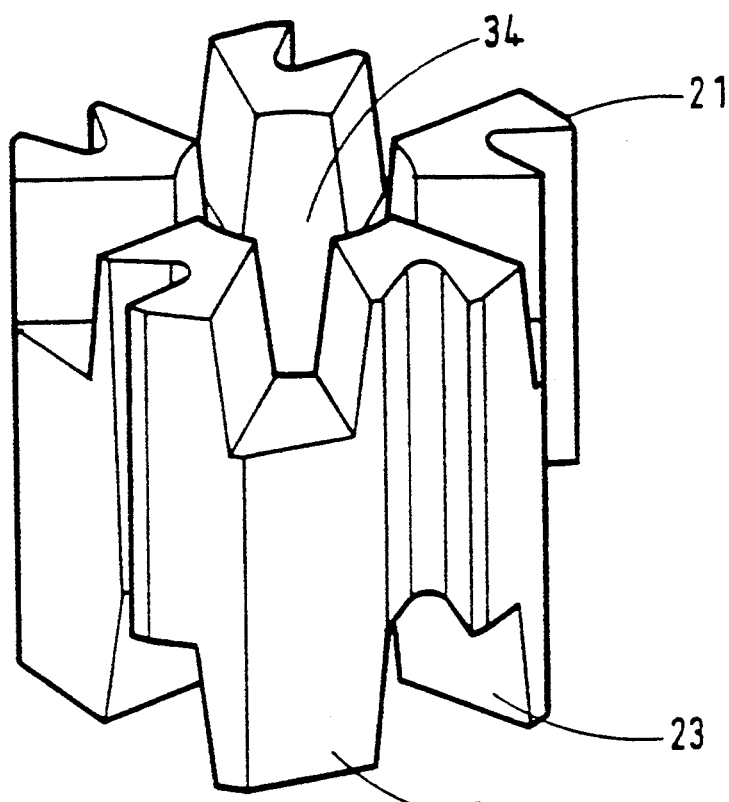
FIG. 2 is a perspective view of one of the cutting teeth on an enlarged scale.
Figure 2A:
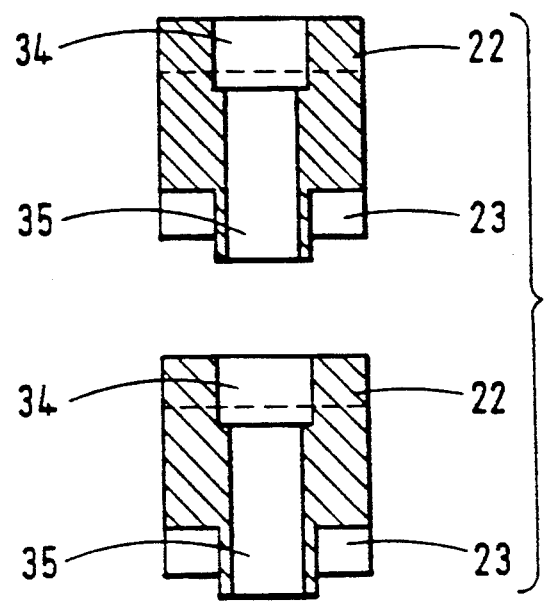
FIG. 2A is a sectional view on a smaller scale of two teeth as shown in FIG. 2.

Referring to FIGS. 2 and 2A, each of the reel% has lateral cutting surfaces 21 which may be of any desired shape or number per tooth. The cutting teeth are geared together by projecting dog-like teeth and recesses 22 and 23, and preferably there is a significant degree of play between teeth 22 and corresponding recesses 23. The cutting teeth may be of any desired height and number, but conveniently in instruments for cutting cavities in bone for joint implants, teeth are typically 5 to 10 mms high and may comprise 10 to 20 teeth in each tool. One further provision is made whereby the teeth can only be inserted over the curved rod with correct orientation by providing a recess 34 at one end of the tooth and a lip-like protrusion 35 at the other end as shown in FIG. 2A. On assembly, the lip 35 of one tooth slides into the recess 34 of another tooth, allowing the dog-like teeth 22 and recesses 23 to engage.

It will be appreciated that when the drive shaft 10 is rotated, which typically would be at about 50 to 150 rpm, the teeth are rotated on the fixed rod 1 and, as shown in FIG. 1, the teeth tend to open out on the inside curved surface 13 of the cutting Tool and are forced together on the concave inner surface 14. This arrangement ensures that the cutting surface presented to the bone or other material comprises an essentially continuous helical cutting surface and the tendency therefore is to cut a smoother profile rather than cut a series of grooves running laterally of the cutting assembly. The cutting assembly, comprising the bracket 7, rod 1 and teeth 18 and 18a, may be removable from the framework and replaceable with another cutting assembly having a different number of teeth or with a curved fixed supporting rod having a different degree of curvature. However, it may be preferable for the surgeon to make use of a plurality of similar tools having different extents of curvature and a variety of different types of cutting teeth.

Figure 3:
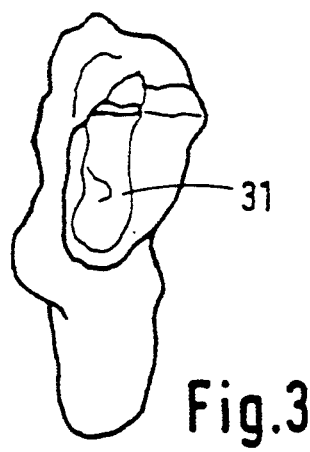
FIG. 3 is a top view of a resectioned hip bone.
Figure 3A:
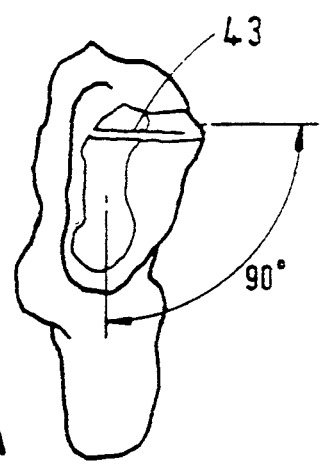
FIG. 3A is a view similar to FIG. 3 showing the anterior profile to be reamed.
Figure 4:
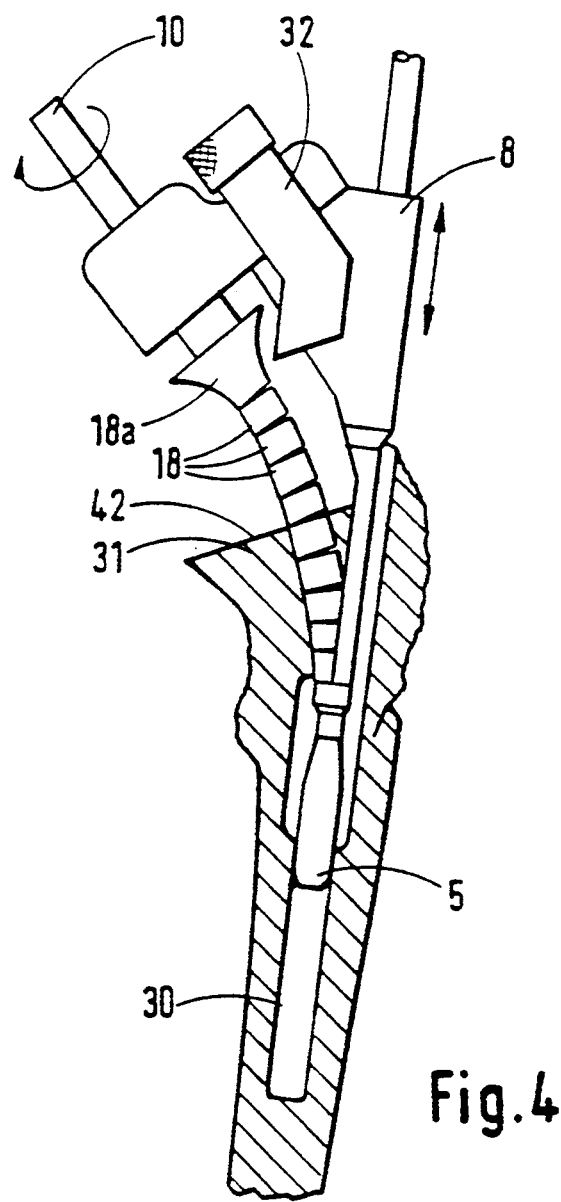
FIG. 4 is a schematic side elevation showing the reaming of the menial profile using the instrument.
Figure 4A:
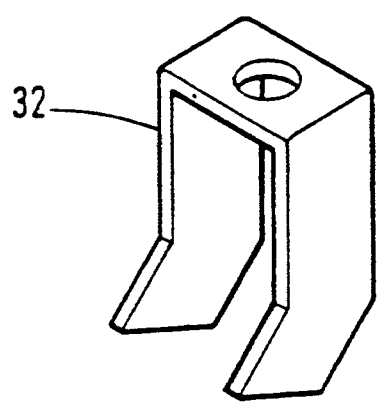
FIG. 4A is a perspective view on an enlarged scale of the depth gauge shown in the instrument of FIG. 4.
Figure 5:
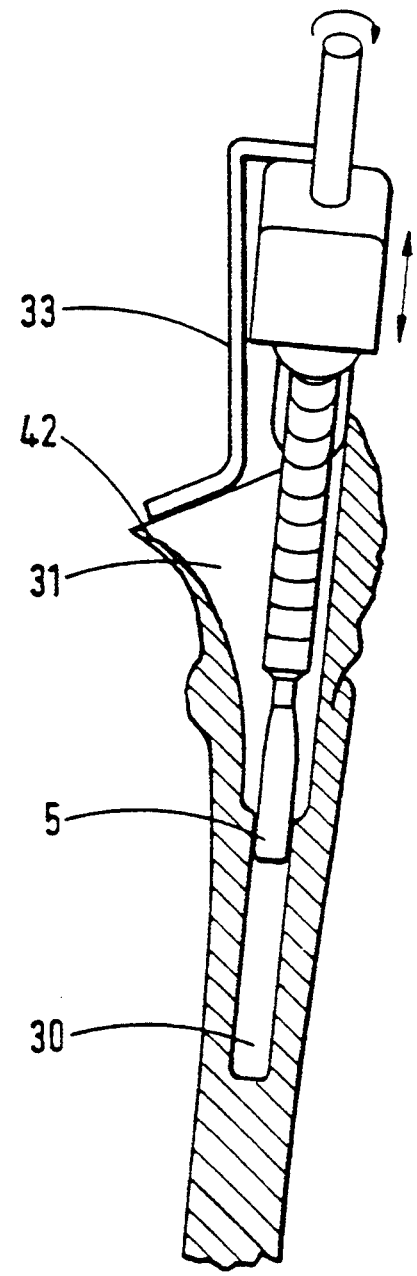
FIG. 5 is a view taken similar to FIG. 4 showing the method of reaming the anterior profile.

One method of using the instrument is illustrated in FIGS. 3 to 5 for the purpose of cutting a profile in a bone canal for a hip implant. The hip implant may be of the kind described in British Patent Application No. 8921008.2 (Publication No. 2236679) and U.S. Pat. No. 4,936,862. For this purpose it is necessary to cut a medial profile and an anterior profile approximately at 90° to each other as illustrated in FIGS. 3 and 3A. The first step is to drill a hole 30 in the bone canal to receive the stem of the implant using a conventional bone drill. This bore 30 is used to guide the cylindrical stud 5 of the frame of the instrument. The instrument according to the invention is then inserted into the resulting canal as shown in FIGS. 4 and 5. As showing in FIG. 4, the medial profile 31 is cut by moving the tool downwardly into the bone while simultaneously rotating the drive connection 10 of the instrument. Cutting is continued until a mediat profile of desired shape is cut as indicated at 31 in FIGS. 3 and 5. An adjustable depth stop 32 is provided on the tool to contact the top 42 of the resectioned bone and to prevent further downward movement of the instrument when the desired depth has been cut. The anterior profile 43 may then be cut as shown in FIG. 5 and, for this purpose, a second depth stop 33 (which may also be adjustable) is provided which likewise contacts the top of the resectioned head of the bone when the correct depth has been machined. Because the instrument is intended for surgical use, metallic parts are preferably manufactured from a non-corrosive metal such as stainless steel.

Referring to FIGS. 6 and 6A, the same reference numerals are used as in FIG. 1 to indicate like components. A flexible drive 61 is linked to connector 19 which is received in a housing 62. A bolt 9 releasably fastens the housing 62 onto the support rod 3. As described in connection with FIG. 1, connector 19 is drivably connected to uppermost conical-shaped tooth 18A. For the purpose of cleaning the teeth, housing 62 is removed by unscrewing the bolt 9. The teeth may then be removed with the guide rod. A grommet 63 at one end of the assembly prevents the teeth sliding off the rod. They can be satisfactorily cleaned without removing them from the rod.

Guide stop 32 defines the line of transection when reaming the medial profile. The depth of cut is adjustable by removing the guide stop 32 and replacing the guide stop with one having a different length. A bolt 64 is provided for this purpose.

FIG. 6A shows the location of the guide stop 33 for determining the depth of cut when reaming the anterior profile. As shown in FIG. 6A, the guide stop can be fitted to the left or right hand side of the instrument by means of the bolt 65 depending on whether the cavity of the left or right femur is being reamed.

Stud 5 is fitted with a tubular adjustment sleeve 66 which is retained on the end of stud 5 by screw thread 67. Sleeve 66 includes an integral knurled nut 68 and a number of interchangeable sleeves, having effective diameters which vary in 1 mm steps, may be provided with the instrument. In this way, the distal end of the support rod can be adjusted for bone canals 30 of different diameters. Each sleeve 66 is formed with opposed apertures 69 which have two purposes. First, they provide flats onto which a spanner may be applied. Secondly, the apertures facilitate cleaning when the sleeve is removed to clean the instrument. As can be seen in FIG. 6A, sleeve 66 is slightly barrel-shaped. This permits the tubular rod 3 to be tilted by about 2-3° and gives the surgeon scope for slight adjustment of the angle of operating the reaming tool.

While the instrument of the present invention has been described with particular reference to its use in cutting and shaping bone canals, it will be appreciated that other uses include other surgical, dental and veterinary applications where there is a need to cut and shape bone, teeth or other hard horny material.

I claim:

1. A surgical instrument for shaping a bone or cavity which comprises a curved rod whose curvature corresponds in one plane to that of a desired surface to be shaped for said bone or cavity, a plurality of cutting heads, each of which having a plurality of cutting surfaces, said cutting heads being individually and sequentially mounted on said rod lengthwise thereof so as to be rotatable thereon and to provide said cutting surfaces lengthwise of the rod, said cutting heads being drivably interconnected so that rotation of one of said heads causes a head adjacent to said one of said heads to rotate.

2. An instrument according to claim 1 wherein said curved rod is mounted in a frame, which includes a guide for location in or on a portion of said bone which serves as a reference surface, said guide limiting the depth of cut of the instrument.

3. An instrument according to claim 1 or 2 wherein the cutting heads are arranged as a continuous row and one end of the row is connected to a drive attachment for releasable connection to a driving means.

4. An instrument according to claim 1 wherein the teeth have lateral cutting surfaces.

5. An instrument according to claim 1 wherein said one head is drivably connected to the adjacent head by one or more projections extending lengthwise of the guide rod and which are engageable with one or more recesses in the adjacent head.

6. An instrument according to claim 5 wherein the or each projection engages in a corresponding recess in the adjacent head with a degree of play, so that the cutting heads together describe a helical-like path when they are rotated.

7. An instrument according to claim 5 wherein said heads are drivably connected to a driving means via a flexible drive.

8. An instrument for shaping a bone cavity which comprises a support rod, a curved guide rod whose curvature corresponds in one plane to that of a desired surface to be shaped for said bone mounted at one end on the support rod and extending generally at an acute angle thereto and a plurality of individual cutting heads mounted sequentially for rotation on said guide rod, each of said heads having lateral cutting surfaces and said heads being drivably interconnected so that rotation of one of said head causes a head adjacent said one of said heads to rotate and to ream an interior of the bone cavity.

9. An instrument according to claim 8 wherein the support rod has a stud portion which engages a hole in the bone cavity to stabilize the instrument while reaming the bone cavity.

10. An instrument according to claim 8 wherein the support rod includes a handle for stabilizing the instrument while reaming the bone cavity.

* * * * *